(12) United States Patent
Bunel et al.

(10) Patent No.: US 7,541,474 B2
(45) Date of Patent: Jun. 2, 2009

(54) CATALYZED PROCESS OF MAKING C-5-SUBSTITUTED HETEROCYCLIC INHIBITORS OF 11β-HYDROXY STEROID DEHYDROGENASE TYPE 1

(75) Inventors: Emilio Bunel, Thousand Oaks, CA (US); Anil Guram, Oak Park, CA (US); Qingyian Liu, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 142 days.

(21) Appl. No.: 11/590,922

(22) Filed: Nov. 1, 2006

(65) Prior Publication Data

US 2007/0117985 A1    May 24, 2007

Related U.S. Application Data

(60) Provisional application No. 60/738,574, filed on Nov. 22, 2005.

(51) Int. Cl.
C07D 277/08    (2006.01)
C07D 263/08    (2006.01)

(52) U.S. Cl. ........................ 548/184; 548/225

(58) Field of Classification Search ................ 548/182, 548/183, 184, 190, 200, 225, 226, 230, 233, 548/316.4, 316.7, 326.5, 333.5, 530, 544, 548/558

See application file for complete search history.

(56) References Cited

FOREIGN PATENT DOCUMENTS

WO    WO 2005/116002 A2    12/2005
WO    WO 2007/061600 A1    5/2007

OTHER PUBLICATIONS

Vippagunta et al., Crystalline solids, 2001, Advanced Drug Delivery Reviews, 48, pp. 3 and 18.*
Lee, et al., "Palladium-Catalyzed α-Arylation of Esters and Protected Amino Acids," J. Am. Chem. Soc., vol. 123, pp. 8410-8411, 2001.
Splelvogel, et al., "Nickel-BINAP Catalyzed Enantioselective α-Arylation of α-Substituted γ-Butyrolactones," J. Am. Chem. Soc., vol. 124, pp. 3500-3501, 2002.
Hamada, et al., "An Improved Catalyst for the Asymmetric Arylation of Ketone Enolates," J. Am. Chem. Soc., vol. 124, No. 7, pp. 1261-1268, 2002.
Kawatsura, et al., "Simple, Highly Active Palladium Catalysts for Ketone and Malonate Arylation: Dissecting the Importance of Chelation and Steric Hindrance," J. Am. Chem. Soc., vol. 121, pp. 1473-1478, 1999.
Stauffer, et al., Palladium-Catalyzed Arylation of Ethyl Cyanoacetate, Fluorescence Reasonance Energy Transfer as a Tool for Reaction Discovery, J. Am. Chem. Soc., vol. 123, pp. 4641-4642, 2001.
Metzger et al., "Comportement et reactivite d'heterocycloammoniums dans la synthese des colorants cyanines et carbocyanines," Bulletin de la Societe Chimique de France, 1967, pp. 30-40 (XP009081230).
Patnaik et al., "Preparation of Some 5-Substituted 2-arylimino-4-thiazolidines," J. Indian Chem. Soc., vol. 34, No. 11, 1957, pp. 814-816, (XP009081229).

* cited by examiner

*Primary Examiner*—Kamal A Saeed
*Assistant Examiner*—Kristin Bianchi
(74) *Attorney, Agent, or Firm*—Foley & Lardner LLP

(57) ABSTRACT

The invention provides a process for preparing 11 β-hydroxy steroid dehydrogenase type 1 inhibitors of formula 2 via a catalyzed reaction between a compound of formula 1 and a compound of formula $R^2LG$ in the presence of base:

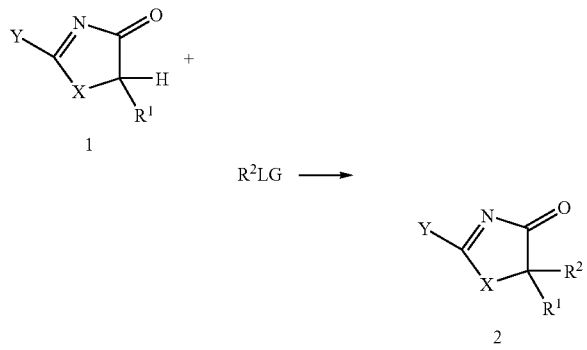

where $R^1$, $R^2$, X, Y, and LG are described in the specification. Exemplary catalysts contain palladium and one or more phosphine ligands. The process can be performed in a stereoselective manner to give enantiomerically enriched products.

34 Claims, No Drawings

CATALYZED PROCESS OF MAKING C-5-SUBSTITUTED HETEROCYCLIC INHIBITORS OF 11β-HYDROXY STEROID DEHYDROGENASE TYPE 1

This regular U.S. utility application claims priority to U.S. Provisional Application Ser. No. 60/738,574, which was filed on Nov. 22, 2005, and which is incorporated herein by reference in its entirety.

BACKGROUND OF THE INVENTION

The present invention relates generally to novel organic synthetic methodology and its application for providing compounds that are useful as inhibitors of 11β-hydroxy steroid dehydrogenase type 1.

Hydroxysteroid dehydrogenases (HSDs) regulate the occupancy and activation of steroid hormone receptors by converting steroid hormones into their inactive metabolites. For a recent review, see Nobel et al., Eur. J. Biochem. 2001, 268:4113-4125.

There exist numerous classes of HSDs. The 11-beta-hydroxysteroid dehydrogenases (11β-HSDs) catalyze the interconversion of active glucocorticoids (such as cortisol and corticosterone), and their inert forms (such as cortisone and 11-dehydrocorticosterone). The isoform 11-beta-hydroxysteroid dehydrogenase type 1 (11β-HSD1) is expressed in liver, adipose tissue, brain, lung and other glucocorticoid tissue and is a potential target for therapy directed at numerous disorders that may be ameliorated by reduction of glucocorticoid action, such as diabetes, obesity and age-related cognitive dysfunction. Seckl, et al., Endocrinology, 2001, 142:1371-1376.

The various isozymes of the 17-beta-hydroxysteroid dehydrogenases (17β-HSDs) bind to androgen receptors or estrogen receptors and catalyze the interconversion of various sex hormones including estradiol/estrone and testosterone/androstenedione. To date, six isozymes have been identifed in humans and are expressed in various human tissues including endometrial tissue, breast tissue, colon tissue, and in the testes. 17-beta-Hydroxysteroid dehydrogenase type 2 (17β-HSD2) is expressed in human endometrium and its activity has been reported to be linked to cervical cancer. Kitawaki et al., J. Clin. Endocrin. Metab., 2000, 85:1371-3292-3296. 17-beta-Hydroxysteroid dehydrogenase type 3 (17β-HSD3) is expressed in the testes and its modulation may be useful for the treatment of androgen-related disorders.

Androgens and estrogens are active in their 17β-hydroxy configurations, whereas their 17-keto derivatives do not bind to androgen and estrogen receptors and are thus inactive. The conversion between the active and inactive forms (estradiol/estrone and testosterone/androstenedione) of sex hormones is catalyzed by members of the 17β-HSD family. 17β-HSD1 catalyzes the formation of estradiol in breast tissue, which is important for the growth of malignant breast tumors. Labrie et al., Mol. Cell. Endocrinol. 1991, 78:C113-C118. A similar role has been suggested for 17β-HSD4 in colon cancer. English et al., J. Clin. Endocrinol. Metab. 1999, 84:2080-2085. 17β-HSD3 is almost exclusively expressed in the testes and converts androstenedione into testosterone. Deficiency of this enzyme during fetal develoment leads to male pseudohermaphroditism. Geissler et al., Nat. Genet. 1994, 7:34-39. Both 17β-HSD3 and various 3α-HSD isozymes are involved in complex metabolic pathways which lead to androgen shuffles between inactive and active forms. Penning et al., Biochem. J. 2000, 351:67-77. Thus, modulation of certain HSDs can have potentially beneficial effects in the treatment of androgen- and estrogen-related disorders.

The 20-alpha-hydroxysteroid dehydrogenases (20α-HSDs) catalyze the interconversion of progestins (such as between progesterone and 20α-hydroxy progesterone). Other substrates for 20α-HSDs include 17α-hydroxypregnenolone or 17α-hydroxyprogesterone, leading to 20α-OH steroids. Several 20α-HSD isoforms have been identified and 20α-HSDs are expressed in various tissues, including the placenta, ovaries, testes and adrenals. Peltoketo, et al., J. Mol. Endocrinol. 1999, 23:1-11.

The 3-alpha-hydroxysteroid dehydrogenases (3α-HSDs) catalyze the interconversion of the androgens dihydrotestosterone (DHT) and 5α-androstane-3α;17β-diol and the interconversion of the androgens DHEA and androstenedione and therefore play an important role in androgen metabolism. Ge et al., Biology of Reproduction 1999, 60:855-860.

Inhibitors of 11β-HSD1, and in particular C5-substituted 2-amino thiazolinones as shown below, have been linked to the treatment of a variety of diseases.

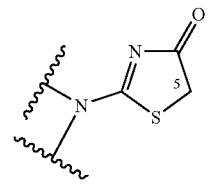

The diseases include, for example, diabetes, obesity and related cardiovascular risk factors, cognitive diseases such as dementia, immunomodulation disorders, glaucoma, and inflammatory diseases. See U.S. patent application No. Ser. 11/135,662, filed on May 24, 2005.

A subset of such inhibitors features unsaturated C-5 substituents, such as aryl groups, which can be introduced in principle via lengthy and traditional syntheses onto parent 2-amino thiazolinones. The diversity of available aryl substrates in particular for C-5 arylation would portend a ready library of C5-aryl substituted 2-amino thiazolinones. However, the existing synthetic methodology for installing the aryl substituent hampers efficient structure-activity relationship (SAR) studies, thereby rendering extant methods not practical in the discovery of 11β-HSD1 inhibitors.

Metal-catalyzed α-arylation of carbonyl compounds would generally suggest a more direct and potentially more efficient route to the desired C5-arylated 2-amino thiazolinones. See S. Lee et al. J. Am. Chem Soc. (2001) 123, 8410-8411; T. Hamada et al. J Am. Chem. Soc. (2002) 124, 1261-1268; M. Kawatsura et al. J Am. Chem. Soc.(1999) 121, 1473-1478; and S. R. Stauffer et al. J. Am. Chem. Soc. (2001), 123, 4641-4642. However, the arylation of heterocycles is relatively unexplored, and the 2-amino thiazolinone scaffold in particular poses regiospecificity problems by virtue of the presence of multiple candidate reaction sites in addition to the desired C-5 position:

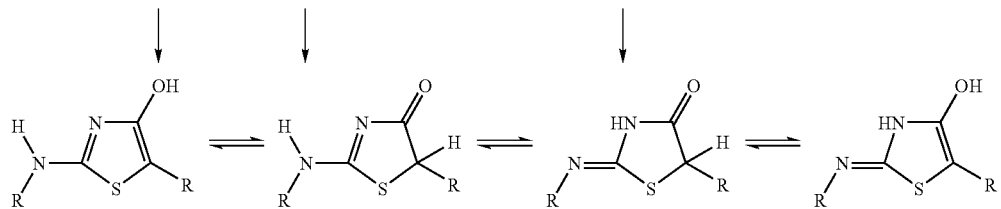

Therefore, a need exists for a relatively short and efficient method to regioselectively derivatize, and in particulate arylate, a 2-amino thiazolinone at the C-5 position.

SUMMARY OF THE INVENTION

The present invention satisfies this need and others by providing a process for the preparation of a compound of formula 2, or a tautomer, stereoisomer, solvate, or pharmaceutically acceptable salt thereof:

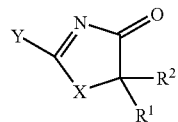

The process comprises reacting a compound of formula 1:

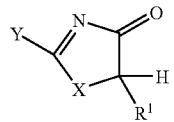

with a compound of formula $R^2LG$ in the presence of a base and a catalyst comprising a transition metal or ion thereof. Variables:

X is selected from the group consisting of S, O, NR, and CRR';

Y is selected from the group consisting of NRR', OR, $C(R)_2R'$, and SR;

LG is a leaving group;

R and R' are independently selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$ alkyl, $(C_1-C_8)$fluoroalkyl $(C_1-C_8)$fluoroalkyl, $(C_1-C_8)$ hydroxyalkyl, $(C_3-C_8)$cycloalkyl, $(C_3-C_8)$ heterocycloalkyl, heteroaryl, aryl, $(C_3-C_8)$cycloalkyl $(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl;

$R^1$ is selected from the group consisting of hydrogen, $(C_1-C_8)$alkyl, $(C_2-C_8)$alkenyl, $(C_2-C_8)$alkynyl, $(C_1-C_4)$ alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$ heterocycloalkyl, heteroaryl, aryl, $(C_3-C_8)$cycloalkyl $(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl, NRR', OR, SR; and $R_2$ is selected $(C_2-C_8)$alkenyl, $(C_2-C_8)$alkynyl, heteroaryl, and aryl.

Each of R, R', $R_1$, and $R^2$, independently of each other, is optionally substituted with one or more substituents selected from the group consisting of oxo, aryl$(C_1-C_4)$alkyl, heteroaryl$(C_1-C_4)$alkyl, halo, cyano, nitro, $(C_1-C_8)$alkyl, $(C_2-C_8)$alkenyl, $(C_2-C_8)$alkynyl, $(C_1-C_8)$alkoxy, $(C_1-C_8)$fluoroalkyl, $(C_2-C_8)$hydroxyalkyl, —C(O)$R^a$, —C(O)O$R^a$, —N$R^a$C(O)O$R^b$, —O$R^a$, —S$R^a$, —OC(O)$R^a$, —C(O)N($R^a$)$_2$, —S(O)$R^a$, —SO$_2R^a$, —SO$_2$N($R^a$)$_2$, —N($R^a$)$_2$ and —N$R^a$C(O)$R^b$.

Substituents $R^a$ and $R^b$ are independently selected from the group consisting of hydrogen and an unsubstituted member selected from $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$fluoroalkyl, $(C_2-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl $(C_1-C_6)$alkyl.

DETAILED DESCRIPTION

Definitions

As used herein, the terms have the following meanings:

The term "alkyl" as used herein refers to a straight or branched chain, saturated hydrocarbon having the indicated number of carbon atoms. For example, $(C_1-C_6)$alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein throughout.

The term "alkenyl" as used herein refers to a straight or branched chain unsaturated hydrocarbon having the indicated number of carbon atoms and at least one double bond. Examples of a $(C_2-C_8)$alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" as used herein refers to a straight or branched chain unsaturated hydrocarbon having the indicated number of carbon atoms and at least one triple bond. Examples of a $(C_2-C_8)$alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkylene" refers to a divalent alkyl group (e.g., an alkyl group attached to two other moieties, typically as a linking group). Examples of a $(C_1-C_7)$alkylene include —CH₂—, —CH₂CH₂—, —CH₂CH₂CH₂—, —CH₂CH₂CH₂CH₂—, CH₂CH₂CH₂CH₂CH₂—, —CH₂CH₂CH₂CH₂CH₂CH₂—, and —CH₂CH₂CH₂CH₂CH₂CH₂CH₂—, as well as branched versions thereof. An alkylene group can be unsubstituted or optionally substituted with one or more substituents as described herein below.

The term "alkenylene" refers to a divalent alkene group (e.g., an alkene group attached to two other moieties, typically as a linking group). Examples of a (C₂-C₇)alkenylene include —CH═CH—, —CH═CHCH₂—, —CH═CHCH₂CH₂—, —CH═CHCH₂CH₂CH₂—, —CH═CHCH₂CH₂CH₂CH₂—, and —CH═CHCH₂CH₂CH₂CH₂CH₂—, as well as branched versions and structure isomers thereof. An alkenylene group can be unsubstituted or optionally substituted with one or more substituents as described herein below.

The term "alkoxy" as used herein refers to an —O-alkyl group having the indicated number of carbon atoms. For example, a (C₁-C₆)alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl," as used herein, refers to an alkyl group (typically one to six carbon atoms) wherein from one or more of the C₁-C₆ alkyl group's hydrogen atoms is replaced with an amine of formula —N(Rᵃ)₂, wherein each occurrence of Rᵃ is independently —H or (C₁-C₆)alkyl. Examples of aminoalkyl groups include, but are not limited to, —CH₂NH₂, —CH₂CH₂NH₂—, —CH₂CH₂CH₂NH₂, —CH₂CH₂CH₂CH₂NH₂, —CH₂CH₂CH₂CH₂CH₂NH₂, —CH₂CH₂CH₂CH₂CH₂NH₂—CH₂CH₂CH₂N(CH₃)₂, t-butylaminomethyl, isopropylaminomethyl and the like.

The term "aryl" as used herein refers to a 6- to 14-membered monocyclic, bicyclic or tricyclic aromatic hydrocarbon ring system. Examples of an aryl group include phenyl and naphthyl. An aryl group can be unsubstituted or optionally substituted with one or more substituents as described herein below.

The term "cycloalkyl" as used herein refers to a 3- to 14-membered saturated or unsaturated non-aromatic monocyclic, bicyclic or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene. A cycloalkyl group can be unsubstituted or optionally substituted with one or more substituents as described herein below.

The term "halo" as used herein refers to —F, —Cl, —Br or —I.

The term "haloalkyl," as used herein, refers to a C₁-C₆ alkyl group wherein from one or more of the C₁-C₆ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain alkyl, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S can be placed at any position of the heteroalkyl group. Examples include —CH₂—CH₂—O—CH₃, —CH₂—CH₂—NH—CH₃, —CH₂—CH₂—N(CH₃)—CH₃, —CH₂—S—CH₂—CH₃, —CH₂—CH₂—S(O)—CH₃, —CH₂—CH₂—S(O)₂—CH₃, and —CH₂—CH═N—OCH₃. Up to two heteroatoms can be consecutive, such as, for example, —CH₂—NH—OCH₃. When a prefix such as (C₂-C₈) is used to refer to a heteroalkyl group, the number of carbons (2 to 8, in this example) is meant to include the heteroatoms as well. For example, a C₂-heteroalkyl group is meant to include, for example, —CH₂OH (one carbon atom and one heteroatom replacing a carbon atom) and —CH₂SH.

To further illustrate the definition of a heteroalkyl group, where the heteroatom is oxygen, a heteroalkyl group is an oxyalkyl group. For instance, (C₂-C₅)oxyalkyl is meant to include, for example —CH₂—O—CH₃ (a C₃-oxyalkyl group with two carbon atoms and one oxygen replacing a carbon atom), —CH₂CH₂CH₂CH₂OH, and the like.

The term "heteroalkylene" by itself or as part of another substituent means a divalent radical derived from heteroalkyl, as exemplified by —CH₂—CH₂—S—CH₂CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the hydrogen atoms in the alkyl group is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH$_2$, and branched versions thereof.

Substituents for the groups referred to as alkyl, heteroalkyl, alkylene, alkenyl, alkynyl, cycloalkyl, heterocycloalkyl, cycloalkenyl and heterocycloalkenyl can be selected from a variety of groups including: —OR$^a$', =O, =NR$^a$', =N—OR$^a$', —NR$^a$'R$^a$'', —SR$^a$', -halo, —SiR$^a$'R$^a$''R$^a$''', —OC(O)R$^a$', —C(O)R$^a$', —CO$_2$R$^a$', —CONR$^a$''', —OC(O)NR$^a$'R$^a$'', —NR$^a$''C(O)R$^a$', —NR$^a$'''C(O)NR$^a$'R$^a$'', —NR$^a$'''SO$_2$NR$^a$'R$^a$'', —NR$^a$'''CO$_2$R$^a$', —NHC(NH$_2$)=NH, —NR$^a$''C(NH$_2$)=NH, —NHC(NH$_2$)=NR$^a$'—S(O)R$^a$', —SO$_2$R$^a$', —SO$_2$NR$^a$'R$^a$'', —NR$^a$'''SO$_2$R$^a$', —CN and —NO$_2$, in a number ranging from zero to three, with those groups having zero, one or two substituents being exemplary. R$^a$', R$^a$'' and R$^a$''' each independently refer to hydrogen, unsubstituted (C$_1$-C$_8$)alkyl, unsubstituted hetero(C$_1$-C$_8$) alkyl, unsubstituted aryl and aryl substituted with one to three substituents selected from -halo, unsubstituted alkyl, unsubstituted alkoxy, unsubstituted thioalkoxy and unsubstituted aryl(C$_1$-C$_4$)alkyl. When R$^a$' and R$^a$'' are attached to the same nitrogen atom, they can be combined with the nitrogen atom to form a 5-, 6- or 7-membered ring. For example, —NR$^a$'R$^a$'' is meant to include 1-pyrrolidinyl and 4-morpholinyl. Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Exemplary substituents for the alkyl and heteroalkyl radicals include but are not limited to —OR$^a$', =O, —NR$^a$'R$^a$'', —SR$^a$', -halo, —SiR$^a$'R$^a$''R$^a$'''—OC(O)R$^a$', —C(O)R$^a$', —CO$_2$R$^a$', —C(O)NR$^a$'R$^a$'', —OC(O)NR$^a$'R$^a$'', —NR$^a$''C(O)R$^a$', —NR$^a$''CO$_2$R$^a$', —NR$^a$'''SO$_2$NR$^a$'R$^a$'', —S(O)R$^a$', —SO$_2$R$^a$', —SO$_2$NR$^a$'R$^a$'', —NR$^a$'''SO$_2$R$^a$', —CN and —NO$_2$, where R$^a$', R$^a$''', and R$^a$'''' are as defined above. Typical substituents can be selected from: —OR$^a$', =O, —NR$^a$'R$^a$''', -halo, —OC(O)R$^a$', —CO$_2$R$^a$', —C(O)NR$^a$'R$^a$''', —OC(O)NR$^a$'R$^a$''', —NR$^a$'''C(O)R$^a$'—NR$^a$'''CO$_2$R$^a$', —NR$^a$'''SO$_2$NR$^a$'R$^a$''', —SO$_2$R$^a$', —SO$_2$NR$^a$'R$^a$''', —NR$^a$''', SO$_2$R$^a$'—CN and —NO$_2$.

Similarly, substituents for the aryl and heteroaryl groups are varied and selected from: -halo, —OR$^a$', —OC(O)R$^a$', —NR$^a$'R$^a$''', —SR$^a$', —R$^a$', —CN, —NO$_2$, —CO$_2$R$^a$', —C(O)NR$^a$'R$^a$''', —C(O)R$^a$', —OC(O)NR$^a$'R$^a$''', —NR$^a$''C(O)R$^a$', —NR$^a$''CO$_2$R$^a$', —NR$^a$'''C(O)NR$^a$'R$^a$''', —NR$^a$'''SO$_2$NR$^a$'R$^a$''', —NHC(NH$_2$)=NH, —NR$^a$''C(NH$_2$)=NH, —NH—C(NH$_2$)=NR$^a$', —S(O)R$^a$', —SO$_2$R$^a$', —SO$_2$NR$^a$'R$^a$''', —NR$^a$'''SO$_2$R$^a$', —N$_3$, —CH(Ph)$_2$, perfluoroalkoxy and perfluoro(C$_1$-C$_4$)alkyl, in a number ranging from zero to the total number of open valences on the aromatic ring system; and where R$^a$, R$^a$''and R$^a$'''are independently selected from hydrogen, unsubstituted (C$_1$-C$_8$)alkyl, unsubstituted hetero(C$_1$-C$_8$)alkyl, unsubstituted aryl, unsubstituted heteroaryl, unsubstituted aryl(C$_1$-C$_4$)alkyl and unsubstituted aryloxy(C$_1$-C$_4$)alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein throughout may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR$^a$∝— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^a$'—, —S—, —S(O)—, —S(O)$_2$—, or —S(O)$_2$NR$^a$'—. The substituent R$^a$, in —NR$^a$' and —S(O)$_2$NR$^a$'—is selected from hydrogen or unsubstituted (C$_1$-C$_6$)alkyl.

It is to be understood that the substituent —CO$_2$H, as used herein, can be optionally replaced with bioisosteric replacements such as:

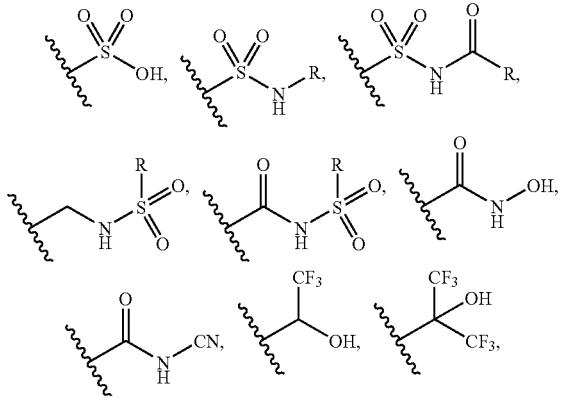

-continued

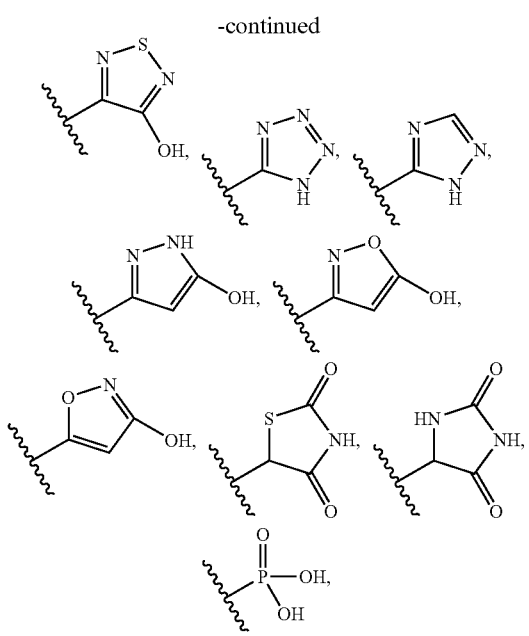

and the like. See, e.g., *The Practice of Medicinal Chemistry*; Wermuth, C. G., Ed.; Academic Press: New York, 1996; p. 203.

The compound of formula 2 can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound of formula 2, including tautomeric forms of the compound.

Certain compounds of formula 2 may have asymmetric centers and therefore exist in different enantiomeric and diastereomeric forms. A compound can exist in the form of an optical isomer or a diastereomer. Accordingly, the invention encompasses compounds of formula 2 in the forms of their optical isomers, diastereomers and mixtures thereof, including racemic mixtures.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of it.

As used herein, the term "solvate" is a form of a compound of Formula 2, where solvent molecules are combined in a definite ratio as an integral part of the crystal structure of the compound.

Depending on its structure, the phrase "pharmaceutically acceptable salt," as used herein, refers to a pharmaceutically acceptable organic or inorganic acid or base salt of a compound of formula 2. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. Furthermore, a pharmaceutically acceptable salt can have more than one charged atom in its structure. In this instance the pharmaceutically acceptable salt can have multiple counterions. Hence, a pharmaceutically acceptable salt can have one or more charged atoms and/or one or more counterions.

Process of Preparation

In one embodiment of the invention, Y is NRR', where R and R' are as defined above. An exemplary embodiment is where R is H.

The skilled artisan will recognize that various heterocycles are represented by formulae 1 and 2. In one embodiment, X is S. In another embodiment, X is O. In still another embodiment, X is NR'. In yet another embodiment, X is CRR'.

In another embodiment, $R^2$ is an optionally substituted heteroaryl or aryl group as defined hereinabove. Thus, in one embodiment, $R^2$ is an optionally substituted aryl group. Exemplary aryl groups are defined above such as, for example, phenyl.

The coupling partner $R^2LG$ contains a leaving group LG. Suitable leaving groups are well-known to those who are skilled in the art. Thus, in one embodiment, LG is selected from the group consisting of Cl, Br, I, —OS(O)$_2$CF$_3$ (triflate), and —OS(O)$_2$(4—CH$_3$-phenyl) (tosylate).

In still another embodiment, X is S, Y is NRR', and $R^2$ is optionally substituted phenyl.

Many transition metal complexes have been reported that can catalyze the direct arylation of a variety of substrates, although, as described above, such substrates generally do not include heterocycles. The skilled artisan therefore will appreciate that a diverse selection of metal-ligand pairings are available to practice the invention, with a given choice guided by a desire to optimize yields and/or enantioselectivity, where applicable. A generally useful catalyst, according to one embodiment of the invention, comprises a transition metal or an ion thereof, where the metal is selected from the group consisting of Co, Rh, Ir, Pd, Ni, Cu.

In another embodiment, the metal is Pd. Thus, for example, the catalyst can comprise a $Pd^{2+}$ ion, i.e., Pd in its formal 2+ oxidation state. In this context, the catalyst can be generated in situ by combining a convenient source of $Pd^0$ optionally with one or more ligands as described below.

Another embodiment provides for the catalyst comprising at least one ligand selected the group consisting of phosphines, amines, carbines, ethers, and combinations thereof. In one embodiment, the ligand is monodentate, and therefore more than one monodentate ligand is typically prescribed for use in the process. The ligands can all be of one type, or they can be mixed. For example, the catalyst may comprise only phosphine ligands or, alternatively, it may comprise phosphine and amine ligands. One embodiment provides for the catalyst comprising at least one phosphine ligand. All of these combinations are contemplated.

In one embodiment, the ligand is multidentate. In accordance with the normal definition in the art, "multidentate" refers to a ligand that coordinates to the transition metal or its ion through two or more atoms. Thus, for example, the ligand can be bidentate or tridentate. Thus, in another embodiment, the ligand is bidentate. An exemplary bidentate ligand is a phosphine that coordinates to the metal or ion through two phosphorus atoms. Other examples of bidentate ligands comprise, for example, various pairings of phosphorus, sulfur, nitrogen, and oxygen donor atoms.

Specific examples of ligands that can be used in the inventive process include but are not limited to:

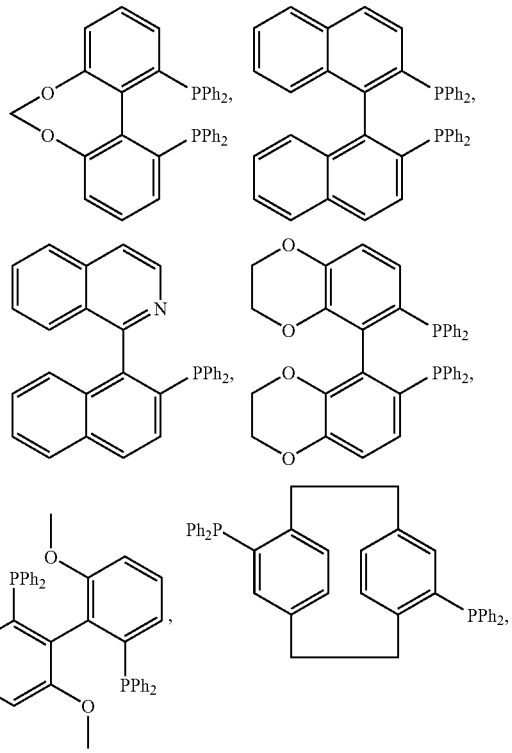

-continued

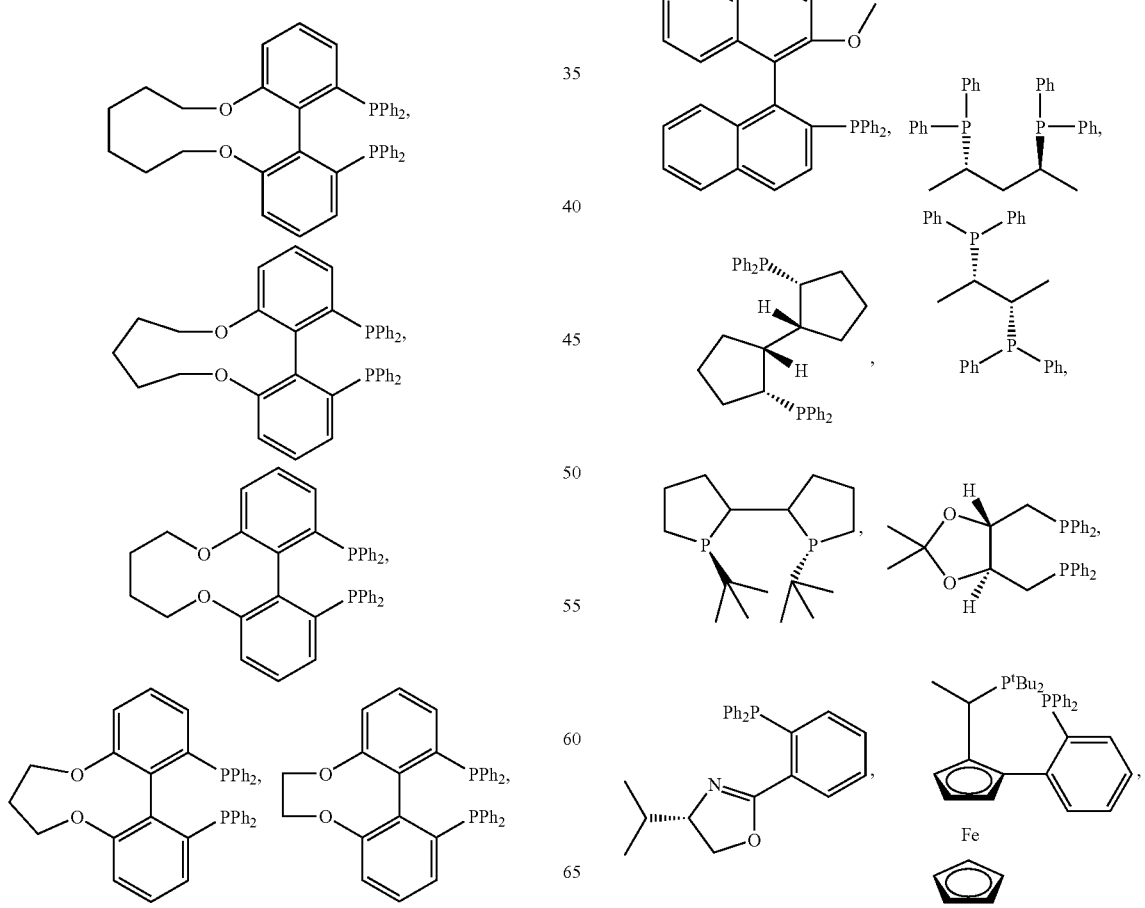

-continued

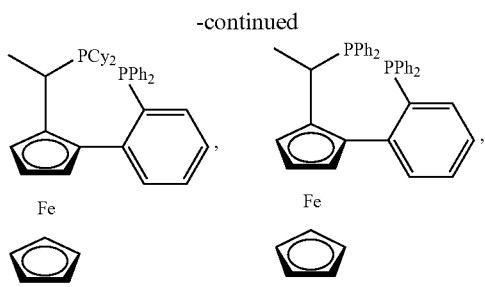

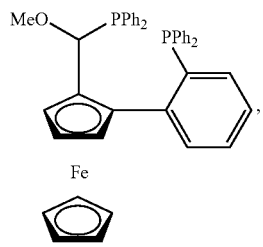

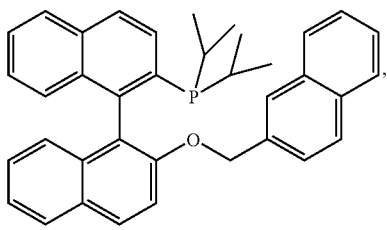

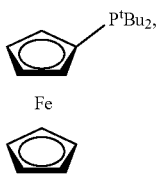

P'Bu₃, and stereoisomers thereof.

In another embodiment, the ligand is selected from bidentate ligands including but not limited to:

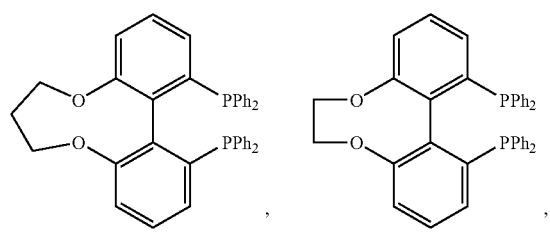

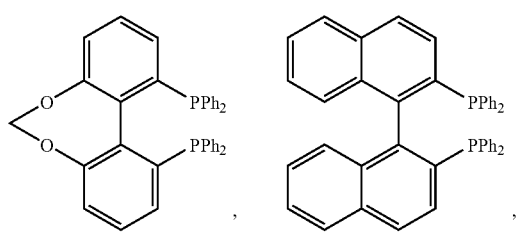

-continued

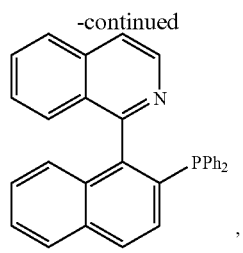

and stereoisomers thereof.

In another embodiment, the ligand is:

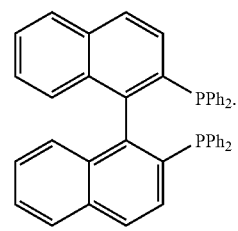

Many of the ligands described herein are capable of existing, or only exist, in certain isomeric forms. For example, some ligands possess one or more chiral centers, and therefore they can exist in stereochemically pure or mixed forms. Other ligands while unbound do not possess chiral centers, but they adopt fixed conformations once coordinated to a metal or ion, and therefore the ligands can impose a stereochemical conformation of the catalyst. The invention expressly contemplates all of these possibilities. Thus, in one embodiment, the catalyst is chiral.

The process also contemplates, in another embodiment, the preparation of a compound of formula 2 where $R^1$ is different from $R^2$. The carbon (C5) to which $R^1$ and $R^2$ are bound therefore can be chiral. Use of a chiral catalyst, as described above, will allow for the preparation of a compound of formula 2 exhibiting an enantiomeric excess by virtue of the stereoselective addition of $R^2$ to C5. The term "enantiomeric excess" is well-defined in the art as the absolute value of the difference between the two enantiomer amounts expressed as a percentage. Thus, for example, the enantiomeric excess can be selected from at least 5%, 10%, 20%, 30%, 40%, 50%, 60%, 70%, 80%, 90%, or 100%. In one embodiment, the enantiomeric excess is at least 40%. In another embodiment, the enantiomeric excess is at least 60%. In still another embodiment, the enantiomeric excess is at least 80%. In another embodiment, the enantiomeric excess is at least 90%. In yet another embodiment, the enantiomeric excess is at least 95%.

Some compounds of formula 2, in addition to exhibiting chirality at C5, may contain one or more other stereochemical centers, and thereby provide for the presence of diastereomers. The invention contemplates the preparation of all such stereochemical isomers of a compound of formula 2.

If needed, further purification and separation of enantiomers and diastereomers can be achieved by routine procedures known in the art. Thus, for example, the separation of enantiomers of a compound of formula 2 can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

As generally described above, the process is performed in the presence of a base. The base can be any convenient organic or inorganic compound. Typically, the base is not nucleophilic. Thus, in one embodiment, the base is selected from carbonates, phosphates, alkoxides, and salts of disilazanes. In another embodiment, the base is a disilazane salt. An exemplary disilazane is hexamethyldisilazane $HN(SiMe_3)_2$. Specific examples of disilazane salts therefore include but are not limited to lithium hexamethyl disilazane and sodium hexamethyl disilazane.

The relative amounts of a compound of formula 1, compound $R^2LG$, catalyst, and base can be conveniently adjusted depending upon, for example, the exact nature of reactants and reaction conditions. Typically the ratios of $R^2LG:1$ and base:1 are greater than or equal to about 1, 1.5, 2, 2.5, or 3.

The amount of catalyst can range in one embodiment from about 0.001% to about 40% based on the amount of the compound of formula 1. In another embodiment, the amount can range from about 1 mol % to about 20 mol%. In another embodiment, the amount can range from about 3 mol % to about 15%. In yet another embodiment, the amount can range from about 5 mol % to about 10%. An exemplary amount of catalyst is about 10%.

The process of the invention, when performed as described herein, can be substantially complete after several minutes to after several hours depending upon the nature and quantity of reactants and reaction temperature, for example. The determination of when the reaction is substantially complete can be conveniently evaluated by ordinary techniques known in the art such as, for example, HPLC, LCMS, TLC, and $^1H$ NMR.

The present invention is not to be limited in scope by the specific embodiments disclosed in the examples, which are intended to be illustrations of a few aspects of the invention, nor is the invention to be limited by any embodiments that are functionally equivalent within the scope of this invention. Indeed, various modifications of the invention in addition to those shown and described herein will become apparent to those skilled in the art and are intended to fall within the scope of the appended claims. To this end, it should be noted that one or more hydrogen atoms or methyl groups can be omitted from the drawn structures consistent with accepted shorthand notation of such organic compounds, and that one skilled in the art of organic chemistry would readily appreciate their presence.

Catalyzed Methods to C-5 Arylated Aminothiazolinones

The following examples illustrate the inventive process as depicted generally by the following scheme:

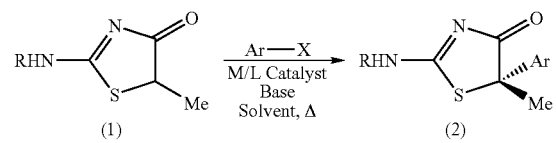

EXAMPLE 1

Synthesis of 4-(5-methyl-4-oxo-2-((S)-1-(2-(trifluoromethyl)phenyl)ethylamino)-4,5-dihydrothiazol-5-yl)benzonitrile (2a)

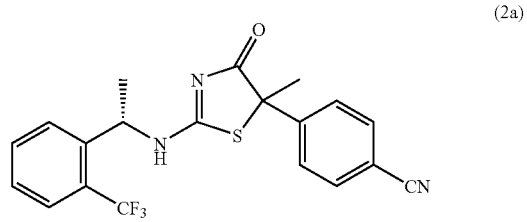

To a mixture of 5-methyl-2-((S)-1-(2-(trifluoromethyl)phenyl)ethylamino)thiazol-4(5H)-one (0.2000 g, 0.662 mmol), 4-bromobenzonitrile (0.301 g, 1.65 mmol), $Pd_2(dba)_3$ (0.0303 g, 0.0331 mmol), (S)-2-(diphenylphosphino)-1-(2-(diphenylphosphino)-naphthalen-1-yl)naphthalene (0.0618 g, 0.0992 mmol), and $LiN(TMS)_2$ (0.277 g, 1.65 mmol) was added toluene (8 mL) in a glove box. The mixture was gradually heated to 95° C. and stirred overnight. The reaction was quenched with $NH_4Cl$ (5 mL), and the reaction mixture was extracted three times with ethylacetate (30 mL). The organic phase was dried over $Na_2SO_4$, filtered and concentrated under vacuum. The crude was purified by chromatography on silica gel using 22% ethylacetate/hexane to remove the impurities and then 36% ethylacetate/hexane to obtain the product as a light yellow solid. MS (ESI, pos. ion) m/z: 404 (M+1), 402 (M-1). $^1H$ NMR ($CDCl_3$, 400 MHz): δ1.71-1.78 (m, 3H), 1.98-2.09 (m, 3H), 5.05 (q, J=8 Hz, 1H), 7.39-7.68 (m, 7H), 7.84 (d, J=8 Hz, 1H), 10.97 (s, 1H). % de (by $^1H$ NMR): 48%.

EXAMPLE 2

Synthesis of 4-(2-((S)-1-(2-fluorophenyl)ethylamino)-5-methyl-4-oxo-4,5-dihydrothiazol-5-yl)benzonitrile (2b)

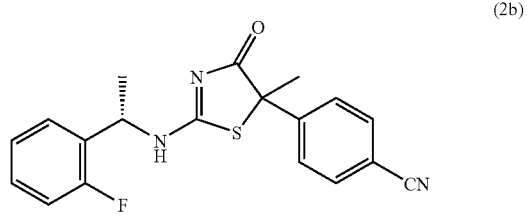

The title compound was prepared from the reaction of 5-methyl-2-((S)-1-(2-fluorophenyl)ethylamino)thiazol-4 (5H)-one with 4-bromobenzonitrile using the procedure described for 2a. MS (ESI, pos. ion) m/z: 354 (M+1).

EXAMPLE 3

Synthesis of 4-(2-((S)-1-(2-chlorophenyl)ethylamino)-5-methyl-4-oxo-4,5-dihydrothiazol-5-yl)benzonitrile (2c)

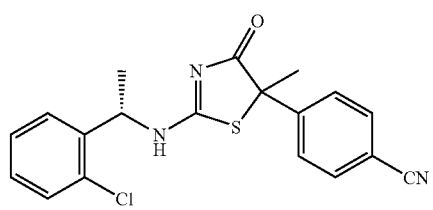

(2c)

The title compound was prepared from the reaction of 5-methyl-2-((S)-1-(2-chlorophenyl)ethylamino)thiazol-4(5H)-one with 4-bromobenzonitrile using the procedure described for 2a. MS (ESI, pos. ion) m/z: 370 (M+1).

EXAMPLE 4

Synthesis of 4-(2-((S)-1-(4-fluorophenyl)ethylamino)-5-methyl-4-oxo-4,5-dihydrothiazol-5-yl)benzonitrile (2d)

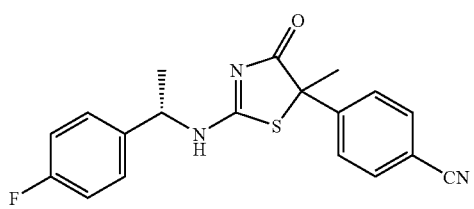

(2d)

The title compound was prepared from the reaction of 5-methyl-2-((S)-1-(4-fluorophenyl)ethylamino)thiazol-4(5H)-one with 4-bromobenzonitrile using the procedure described for 2a. MS (ESI, pos. ion) m/z: 354 (M+1).

EXAMPLE 4

Synthesis of 2-((S)-1-(4-fluorophenyl)ethylamino)-5-(4-(2-hydroxypropan-2-yl)phenyl)-5-methylthiazol-4(5H)-one (2e)

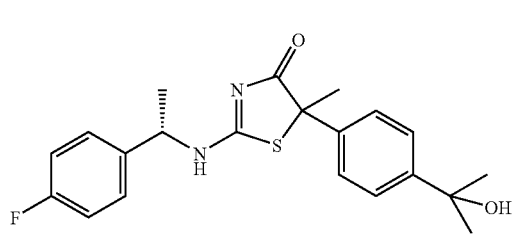

(2e)

The title compound was prepared from the reaction of 5-methyl-2-((S)-1-(4-fluorophenyl)ethylamino)thiazol-4(5H)-one with 2-(4-bromophenyl)propan-2-ol using the procedure described for 2a. 4.0 equivalents of LiN(SiMe$_3$)$_2$ was used. MS (ESI, pos. ion) m/z: 387 (M+1).

EXAMPLE 6

Synthesis of 1-(4-(2-((S)-1-(4-fluorophenyl)ethylamino)-5-methyl-4-oxo-4,5-dihydrothiazol-5-yl)phenyl)cyclopropanecarbonitrile (2f)

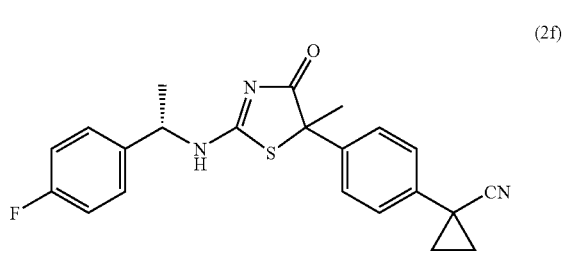

(2f)

The title compound was prepared from the reaction of 5-methyl-2-((S)-1-(4-fluorophenyl)ethylamino)thiazol-4(5H)-one with 1-(4-bromophenyl) cyclopropane carbonitrile using the procedure described for 2a. MS (ESI, pos. ion) m/z: 394 (M+1).

EXAMPLE 7

Synthesis of 2-(bicyclo[2.2.1]heptan-2-ylamino)-5-methyl-5-phenylthiazol-4(5H)-one (2 g)

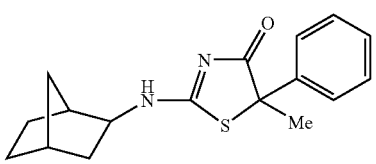

(2g)

The title compound was prepared from the reaction of 2-(bicyclo[2.2.1]heptan-2-ylamino)-5-methylthiazol-4(5H)-one with bromobezene using the procedure described for 2a. MS (ESI, pos. ion) m/z: 301(M+1). % de (chiral LC): 10%.

EXAMPLE 8

Synthesis of 2-(bicyclo[2.2.1]heptan-2-ylamino)-5-methyl-5-(pyridin-4-yl)thiazol-4(5H)-one (2h)

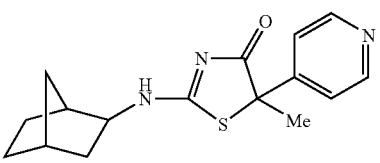

(2h)

The title compound was prepared from the reaction of 2-(bicyclo[2.2.1]heptan-2-ylamino)-5-methylthiazol-4(5H)-one with bromopyridine using the procedure described for 2a. 4.0 equivalent of LiN(SiMe$_3$)$_2$ was used. MS (ESI, pos. ion) m/z: 302 (M+1). % de (chiral LC): 20%

EXAMPLE 9

Synthesis of 4-(2-(bicyclo[2.2.1]heptan-2-ylamino)-5-methyl-4-oxo-4,5-dihydrothiazol-5-yl)benzonitrile (2i)

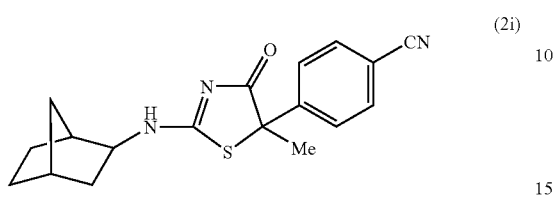

(2i)

The title compound was prepared from the reaction of 2-(bicyclo[2.2.1 ]heptan-2-ylamino)-5-methylthiazol-4(5H)-one with 4-bromobenzonitrile using the procedure described for 2a. MS (ESI, pos. ion) m/z: 326 (M+1).

EXAMPLE 10

Synthesis of Methyl 4-(2-((S)-1-(4-fluorophenyl)ethylamino)-5-methyl-4-oxo-4,5-dihydrothiazol-5-yl)benzoate (2j)

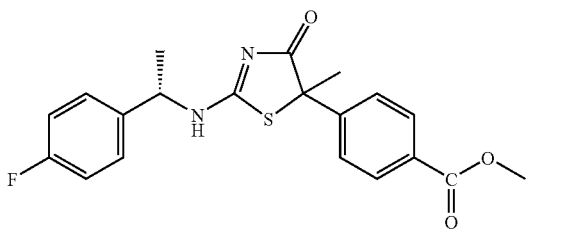

(2j)

The title compound was prepared from the reaction of 5-methyl-2-((S)-1-(4-fluorophenyl)ethylamino)thiazol-4(5H)-one with methyl-4-bromobenzoate using the procedure described for 2a. 2.0 equivalent of NaN(SiMe₃)₂ or LiN(SiMe₃)₂ with reaction temperature of 50° C. was used. MS (ESI, pos. ion) m/z: 387 (M+1).

Synthesis of additional Pharmaceutically Active Compounds

The following examples illustrate transformations of pharmaceutically active compounds (2) described above into additional compounds (3) that can inhibit 11β-hydroxy steroid dehydrogenase type 1 according to the following general scheme:

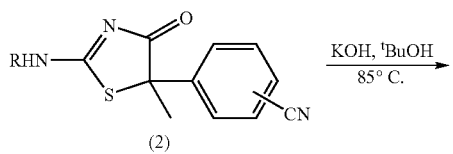

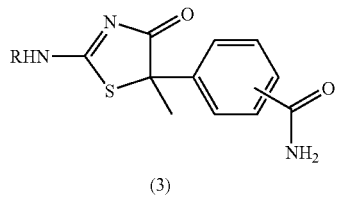

(3)

EXAMPLE 11

Synthesis of 4-(5-methyl-4-oxo-2-((S)-1-(2-(trifluoromethyl)phenyl)ethylamino)-4,5-dihydrothiazol-5-yl)benzamide (3a)

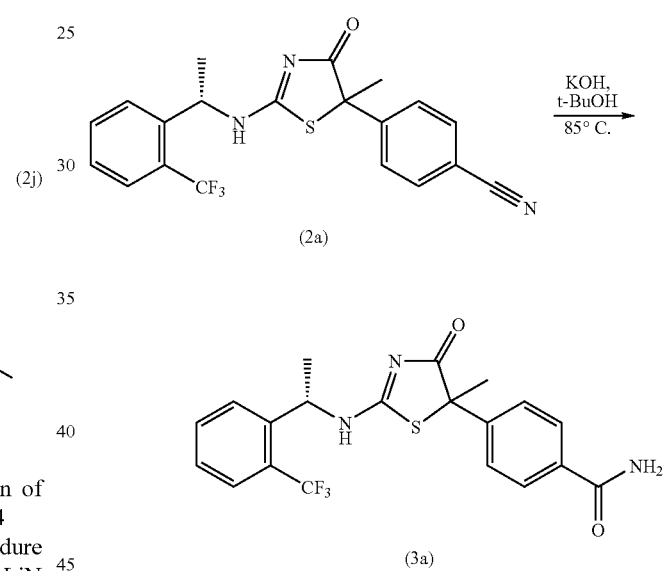

A stirred mixture of 4-(5-methyl-4-oxo-2-((S)-1-(2-(trifluoromethyl)phenyl) ethylamino)-4,5-dihydrothiazol-5-yl) benzonitrile (0.080 g, 0.20 mmol), prepared according to Example 1, and potassium hydroxide (0.14 g, 2.6 mmol) and t-BuOH (2 mL) was gradually heated to 85° C. After 1 h, 2N HCl was added to the reaction mixture until the pH reached 7-8. The reaction mixture was extracted with CH₂Cl₂ three times (50 mL). The organic phase was dried over Na₂SO₄, concentrated in vacuo. The crude product was purified by preparative TLC: 10% MeOH—CH₂Cl₂. The product (3a) was obtained as a white solid. MS (ESI, pos. ion) m/z: 422 (M+1), 420 (M-1). $^1$H NMR (CDCl₃, 400 MHz): δ1.73-1.77 (m, 3H), 1.98, 2.08 (s, 3H), 5.04 (q, J=8 Hz, 1H), 6.17-6.39 (m, 2H), 7.36-7.42 (m, 2H), 7.52-7.75 (m 4H), 7.80-7.86 (m, 2H).

Following the procedure of Example 11, additional compounds 3b-3f were prepared from compounds 2b-2f as shown in the following table:

| Product Compound No. | Final Compound Structure | Reactant Compound No. |
|---|---|---|
| 3b | 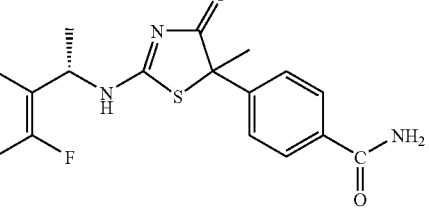 | 2b |
| 3c | 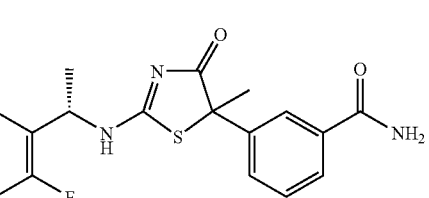 | 2c |
| 3d | 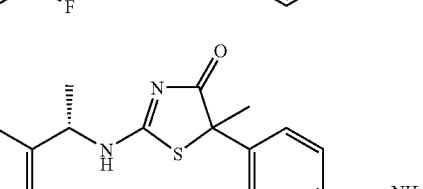 | 2d |
| 3e | 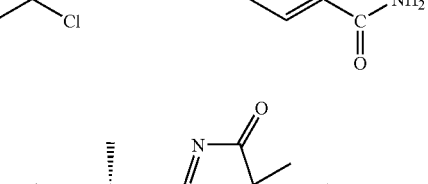 | 2e |
| 3f | 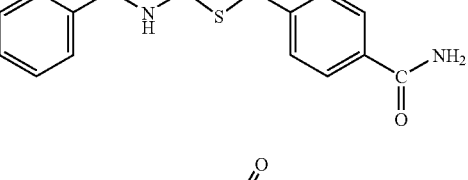 | 2f |

We claim:

1. A process for the preparation of a compound of formula 2, or a tautomer, stereoisomer, or pharmaceutically acceptable salt thereof:

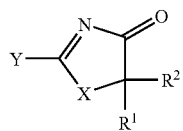

comprising reacting a compound of formula 1:

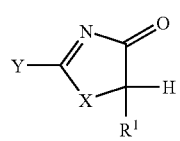

with a compound of formula R²LG in the presence of a base and a catalyst comprising a transition metal or ion thereof, wherein X is selected from S or O;
Y is selected from the group consisting of NRR', OR, C(R)$_2$R', and SR;
LG is a leaving group;
R and R' are independently selected from the group consisting of hydrogen, (C$_1$-C$_8$)alkyl, (C$_2$-C$_8$)alkenyl, (C$_2$-C$_8$)alkynyl, (C$_1$-C$_4$)alkoxy, (,-C$_4$)alkoxy, (C$_1$-C$_4$)alkyl, (C$_1$-C$_8$)fluoroalkyl, (C$_1$-C$_8$)hydroxyalkyl, (C$_3$-C$_8$)cycloalkyl, (C$_3$-C$_8$)heterocycloalkyl, heteroaryl, aryl, (C$_3$-C$_8$)cycloalkyl(C$_1$-C$_6$)alkyl, (C$_3$-C$_8$)heterocycloalkyl(C$_1$-C$_6$)alkyl, heteroaryl(C$_1$-C$_6$)alkyl and aryl(C$_1$-C$_6$)alkyl;
R$^1$ is selected from the group consisting of hydrogen, (C$_1$-C$_8$)alkyl, (C$_2$-C$_8$)alkenyl, (C$_2$-C$_8$)alkynyl, (C$_1$-C$_4$)alkoxy(C$_1$-C$_4$)alkyl, (C$_1$-C$_8$)fluoroalkyl, (C$_1$-C$_8$)hydroxyalkyl, (C$_3$-C$_8$)cycloalkyl, (C$_3$-C$_8$)heterocycloalkyl, heteroaryl, aryl, (C$_3$-C$_8$)cycloalkyl(C$_1$-C$_6$)alkyl, (C$_3$-C$_8$)heterocycloalkyl(C$_1$-C$_6$)alkyl, heteroaryl(C$_1$-C$_6$)alkyl and aryl(C$_1$-C$_6$)alkyl, NRR', OR, and SR;
R$^2$ is selected (C$_2$-C$_8$)alkenyl, (C$_2$-C$_8$)alkynyl, heteroaryl, and aryl; and wherein
each of R, R', R$^1$, and R$^2$ is optionally substituted with one or more substituents selected from the group consisting of oxo, aryl(C$_1$-C$_4$)alkyl, heteroaryl(C$_1$-C$_4$)alkyl, halo, cyano, nitro, (C$_1$-C$_8$)alkyl, (C$_2$-C$_8$)alkenyl, (C$_2$-C$_8$)alkynyl, (C$_1$-C$_8$)alkoxy, (C$_1$-C$_8$)fluoroalkyl, (C$_2$-C$_8$)hydroxyalkyl, -C(O)R$^a$, -C(O)OR$^a$, -NR$^a$C(O)OR$^b$, -OR$^a$, -SR$^a$, -OC(O)R$^a$, -C(O)N(R$^a$)$_2$, -S(O)R$^a$, -SO$_2$R$^a$, -SO$_2$N(R$^a$)$_2$, -N(R$^a$)$_2$ and -NR$^a$C(O)R$^b$;
wherein R$^a$ and R$^b$ are independently selected from the group consisting of hydrogen and an unsubstituted member selected from (C$_1$-C$_8$)alkyl, (C$_2$-C$_8$)alkenyl, (C$_2$-C$_8$)alkynyl, (C$_1$-C$_4$)alkoxy(C$_1$-C$_4$)alkyl, (C$_1$-C$_8$)fluoroalkyl, (C$_2$-C$_8$)hydroxyalkyl, (C$_3$-C$_8$)cycloalkyl, (C$_3$-C$_8$)heterocycloalkyl, heteroaryl, aryl, (C$_3$-C$_8$)cycloalkyl(C$_1$-C$_6$)alkyl, (C$_3$-C$_8$)heterocycloalkyl(C$_1$-C$_6$)alkyl, heteroaryl(C$_1$-C$_6$)alkyl and aryl(C$_1$-C$_6$)alkyl.

2. The process according to claim 1, wherein Y is NRR'.
3. The process according to claim 2, wherein R is H.
4. The process according to claim 1, wherein X is S.
5. The process according to claim 1, wherein R$^2$ is optionally substituted heteroaryl or aryl.
6. The process according to claim 5, wherein R$^2$ is optionally substituted aryl.
7. The process according to claim 6, wherein R$^2$ is optionally substituted phenyl.
8. The process according to claim 1, wherein LG is selected from the group consisting of Cl, Br, I, -OS(O)$_2$CF$_3$, and -OS(O)$_2$(4-CH$_3$-phenyl).
9. The process according to claim 1, wherein
X is S;
Y is NRR'; and
R$^2$ is optionally substituted phenyl.
10. The process according to claim 1, wherein the catalyst comprises a transition metal selected from the group consisting of Co, Rh, Ir, Pd, Ni, Cu, and ions thereof.
11. The process according to claim 10, wherein the transition metal is Pd or an ion thereof.
12. The process according to claim 1, wherein the transition metal catalyst further comprises at least one ligand selected from the group consisting of phosphines, amines, carbines, ethers, and combinations thereof.
13. The process according to claim 12, wherein the ligand is multidentate.

14. The process according to claim 12, wherein the catalyst comprises at least one phosphine ligand.
15. The process according to claim 14, wherein the phosphine ligand is multidentate.
16. The process according to claim 14, wherein the phosphine ligand is bidentate.
17. The process according to claim 14, wherein the catalyst comprises more than one phosphine ligand.
18. The process according to claim 17, wherein the phosphine ligand is monodentate.
19. The process according to claim 12, wherein the ligand is selected from the group consisting of:

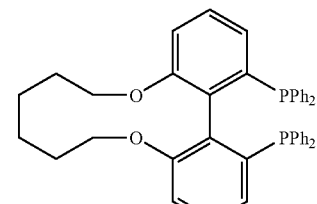

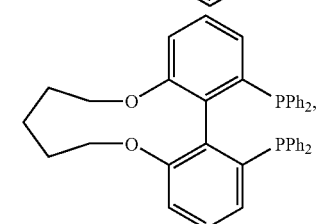

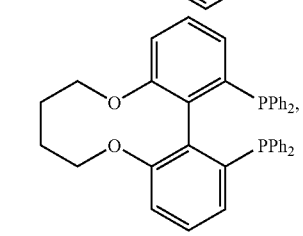

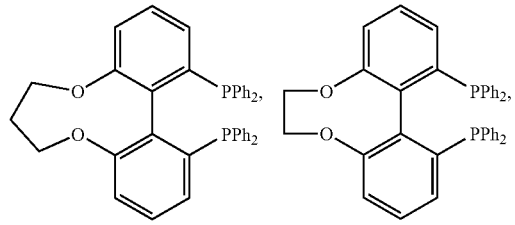

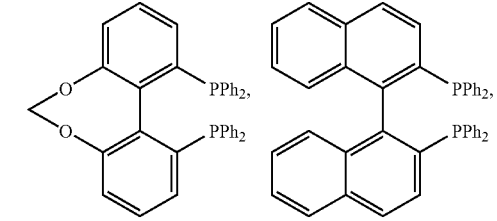

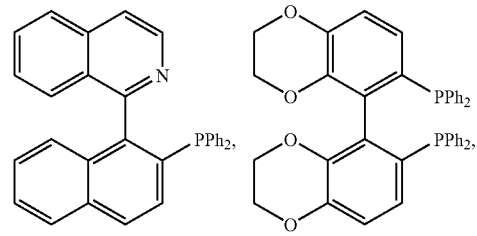

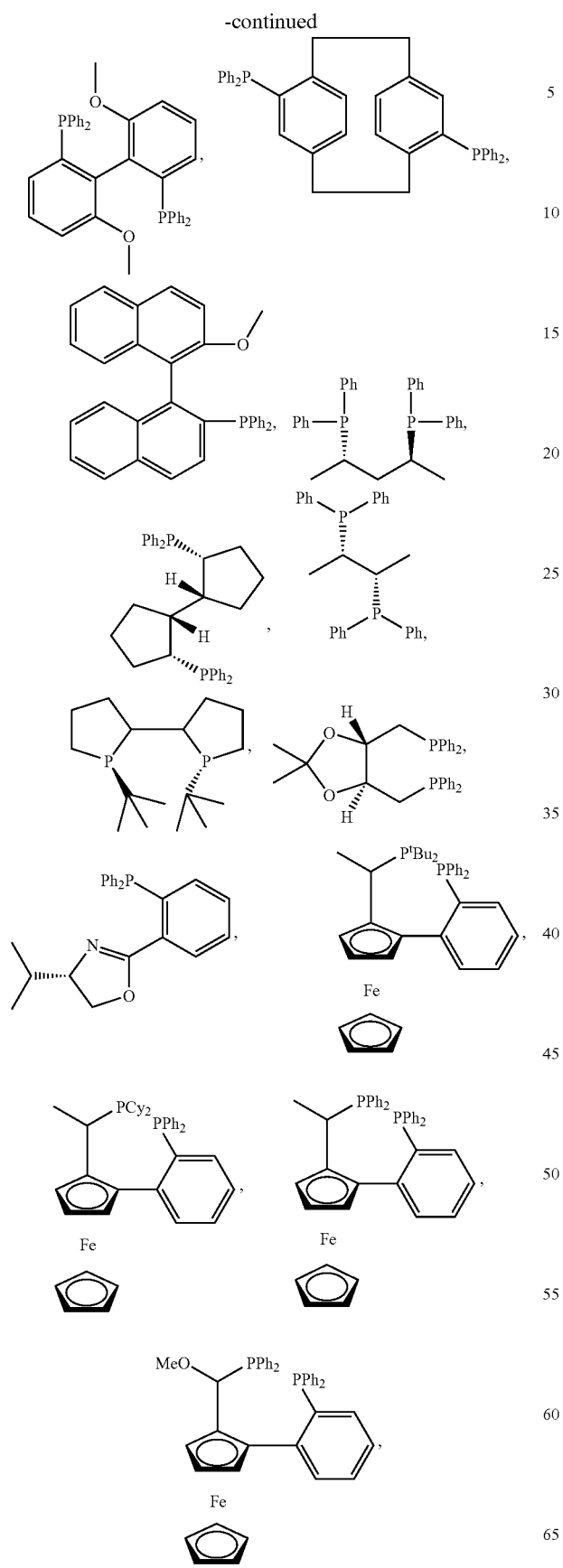
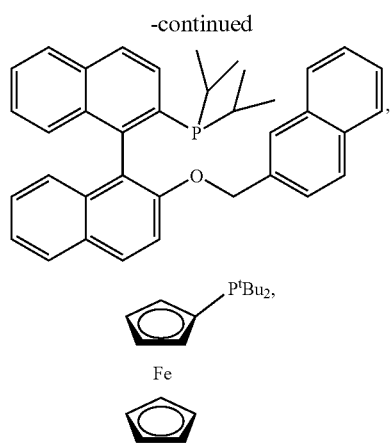
P^tBu_3, and stereoisomers thereof.
20. The process according to claim 19, wherein the ligand is selected from the group consisting of:
and stereoisomers thereof.
21. The process according to claim 20, wherein the ligand is:
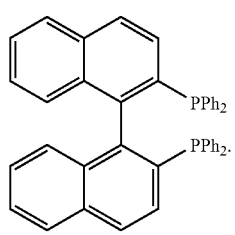

22. The process according to claim 1, wherein the process is performed at a temperature in the range of about 25° C. to about 110° C.

23. The process according to claim 22, wherein the process is performed at a temperature in the range of about 40° C. to about 100° C.

24. The process according to claim 23, wherein the process is performed at a temperature in the range of about 50° C. to about 95° C.

25. The process according to claim 1, wherein the base is selected from the group consisting of carbonates, phosphates, alkoxides, and disilazanes.

26. The process according to claim 25, wherein the base is a disilazane.

27. The process according to claim 26, wherein the base is selected from lithium hexamethyl disilazane and sodium hexamethyl disilazane.

28. The process according to claim 1, wherein $R^1$ is different from $R^2$, whereby the compound of formula 2 is prepared as a mixture of enantiomers.

29. The process according to claim 28, wherein the enantiomeric excess is at least 5%, 10%, 20%, 30%, 40%, 50%, 60%, 70%, 80%, 90%, or 100%.

30. The process according to claim 29, wherein the enantiomeric excess is at least 40%.

31. The process according to claim 30, wherein the enantiomeric excess is at least 60%.

32. The process according to claim 31, wherein the enantiomeric excess is at least 80%.

33. The process according to claim 32, wherein the enantiomeric excess is at least 90%.

34. The process according to claim 33, wherein the enantiomeric excess is at least 95%.

* * * * *